US00PP11659P

United States Patent [19]

Noodelijk

[11] Patent Number: Plant 11,659

[45] Date of Patent: Nov. 28, 2000

[54] CHRYSANTHEMUM PLANT NAMED 'OBERON'

[75] Inventor: Robert Noodelijk, Woubrugge, Netherlands

[73] Assignee: Chrysanthemum Breeders Association N.V., Netherlands

[21] Appl. No.: 09/179,457

[22] Filed: Oct. 27, 1998

[51] Int. Cl.[7] ..... A01H 5/00

[52] U.S. Cl. ..... Plt./287; Plt./286

[58] Field of Search ..... Plt./286, 287, 297, Plt./298, 292, 293

*Primary Examiner*—Howard J. Locker
*Attorney, Agent, or Firm*—Parkhurst & Wendel, LLP

[57] ABSTRACT

A chrysanthemum plant named Oberon characterized by its small sized blooms with greyed-red ray florets and prolific branching early natural season flower date of August 4–7; blooming for a period of 6 weeks.

1 Drawing Sheet

BACKGROUND OF THE INVENTION

The new plant of the present invention comprises a new and distinct cultivar of chrysanthemum plant that is a cross of unknown *Dendranthema grandiflora* parents. The new and distinct cultivar was a seedling resulting from the open pollination among groups of chrysanthemum cultivars maintained under the control of the inventor for breeding purposes. The new and distinct cultivar was discovered and selected as one flowering plant by Rob Noodelijk on a cultivated field in Rijsenhout, Holland in Aug., 1996. The plant has been asexually reproduced by cuttings in greenhouses at Rijsenhout, Holland. The new cultivar has been found to retain its distinctive characteristics through successive propagations.

SUMMARY OF THE INVENTION

The present plant is a new and distinct variety of chrysanthemum of a small sized bloom and greyed-red ray florets.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
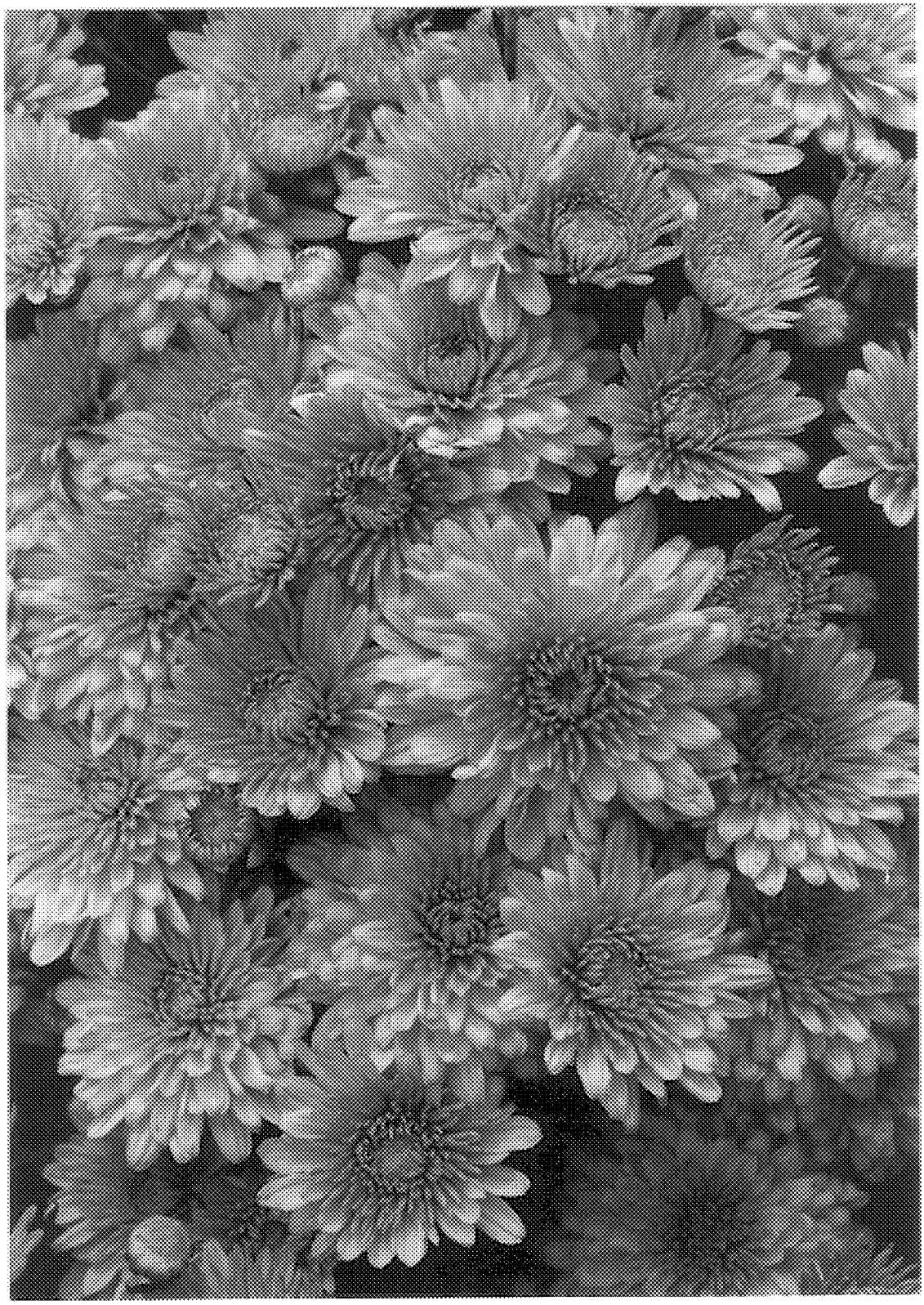
FIG. 1 shows the various stages of bloom of the new cultivar.

This new variety of chrysanthemum is of the botanical classification *Dendranthema grandiflora*. The observations and measurements were gathered from plants grown out doors in Rijsenhout, Holland under natural day length and temperature and planted week 22 in 1997 and 1998. The natural blooming date of this crop was August 4–7 (week 32). The average height of the plants was 20 cms. This new variety produces small sized blooms with greyed-red ray florets and yellow-green disc florets (only visible at an early stage of inflorescence).

The following is a description of the plant and characteristics that distinguish Oberon as a new and distinct variety.

The color designations (color designations are from the R.H.S. Colour Chart) are taken from the plant itself. Accordingly, any discrepancies between the color designa tions and the colors depicted in the photographs are due to photographic tolerances.

Botanical Classification
CULTIVAR Oberon

| | |
|---|---|
| Bud | |
| Size | SMALL CROSS SECTION ± 1.0 CM HEIGHT ±1.0 CM |
| Outside Color | RED 51 D |
| Bloom | |
| Size | SMALL |
| Fully Expanded | 4–4½ CM |
| Borne (number of blooms per branch) | UPPER AND LOWER PORTION PLURAL BLOOMS PER BRANCH (APPROX. 6 BLOOMS) |
| Length of lateral branch | FROM TOP TILL BOTTOM APPROX. 10.0 CM |
| lateral branch, attachment | WEAK |
| Branching | Prolific with 6–8 breaks after pinching |
| Form | DECORATIVE |
| Performance (on the plant) | 6 WEEKS |
| Color | |
| Disc florets | At an early stage of inflorescence, yellow-green |
| Color of the upper surface of the majority of the ray-florets | Greyed-red 179 C near the center, the outer ray florets greyed-red 182 D |
| Color of the lower surface of the majority of the ray-florets | ORANGE 27 B TO GREYED PURPLE 185 D AT THE TIPS |
| Tonality from Distance | A COMPACT GARDEN MUM WITH GREYED-RED BLOOMS AT A MATURE STAGE OF INFLORESCENCE AND A YELLOW-GREEN CENTER IN AN EARLY STAGE OF INFLORESCENCE |
| Discoloration of ray florets | TO GREYED-PURPLE 186 D |

-continued

| Botanical Classification CULTIVAR Oberon | |
|---|---|
| Discoloration of disc florets | To yellow-green 152 C |
| Ray florets | |
| Texture | UPPERSIDE SMOOTH UNDERSIDE SMOOTH |
| Number | ±190–220 |
| Cross-section | FLAT |
| Longitudinal axis of the majority | REFLEXING |
| Shape of tip | ROUND |
| Fragrance | TYPICAL CHRYSANTHEMUM |
| Disc diamter (natural season crop) | 0.7 cm |
| Reproductive Organs | |
| Stamen | None present |
| Pollen | NONE |
| Styles (present in both ray and disc florets) | GREEN, THIN |
| Style Length | ±3 MM |
| Stigmas | YELLOW–GREEN |
| Stigma Width | ±1 MM |
| Ovaries | ENCLOSED IN CALYX |
| Plant | |
| Form | A GARDENMUM (POT MUM) MEANT FOR OUTDOOR USE |
| Growth | SHORT |
| Height (from soil level) | ±20 CM |
| Stem Color | NEAR GREEN 137 D |
| Stem Strength | MEDIUM |

-continued

| Botanical Classification CULTIVAR Oberon | |
|---|---|
| Stem Brittleness | PRESENT |
| Stem Anthocyanin Coloration | NONE |
| Natural blooming date | August 4–7 (week 32) |
| Foliage | |
| Color | UPPERSIDE GREEN 139 A UNDERSIDE GREEN 137 B |
| Size | SMALL: |
| | LENGTH ±6 CM WIDTH ±4 CM |
| Quantity (number per lateral branch) | 10–12 |
| Shape | INCURVED |
| Texture | FLESHY |
| Ribs and Veins | RIBS AND VEINS WELL DEVELOPED |
| Edge | CRENATED |
| Shape of Base of Sinus Between Lateral Lobes | ROUND |
| Margin of Sinus Between Lateral Lobes | CONVERGING |
| Shape of Base | ROUND |
| Apex | MUCRONATE |

I claim:

1. A new and distinct variety of chrysanthemum plant as described and illustrated.

* * * * *